United States Patent [19]
Park et al.

[11] Patent Number: 5,371,275
[45] Date of Patent: Dec. 6, 1994

[54] METHODS FOR PREPARING ETHYLIDENE DIACETATE

[75] Inventors: Dae C. Park; Sung Y. Cho, both of Daejonjikhal, Rep. of Korea

[73] Assignee: Korean Research Institute of Chemical Technology, Daejonjikhal, Rep. of Korea

[21] Appl. No.: 97,370

[22] Filed: Jul. 23, 1993

Related U.S. Application Data

[62] Division of Ser. No. 772,256, Oct. 7, 1991, abandoned.

Foreign Application Priority Data

Oct. 5, 1990 [KR] Rep. of Korea ............... 15830/1990

[51] Int. Cl.$^5$ .............................................. C07C 67/36
[52] U.S. Cl. ..................................................... 560/232
[58] Field of Search .......................................... 560/232

[56] References Cited

U.S. PATENT DOCUMENTS

| | | | |
|---|---|---|---|
| 3,714,185 | 1/1973 | McCoy et al. | 260/326.5 FN |
| 3,940,432 | 2/1976 | Walker et al. | 260/449 R |
| 4,133,776 | 1/1979 | Pruett et al. | 252/431 N |
| 4,246,183 | 1/1981 | Knifton | 260/408 |
| 4,411,820 | 10/1983 | Pretzer et al. | 502/167 |
| 4,690,912 | 9/1987 | Paulik et al. | 502/161 |
| 4,810,821 | 3/1989 | Paulik et al. | 560/232 |

OTHER PUBLICATIONS

Rideal, Concepts in Catalysis, 1968, Pub. by Academic Press, New York, N.Y., pp. 4–5.

*Primary Examiner*—Arthur C. Prescott
*Attorney, Agent, or Firm*—Browning, Bushman, Anderson & Brookhart

[57] ABSTRACT

The present invention relates to a process for preparing a catalyst useful in producing ethylidene diacetate and to a process for producing ethylidene diacetate by a continuous process using the catalyst prepared. In the preparation of ethylidene diacetate from carbon monoxide and hydrogen, the conventional preparation method using a homogeneous catalyst system comprising a transition metal catalyst is hampered by difficulty in separating the catalyst from the reaction product after completion of the reaction. The catalyst of the present invention is separated easily from the reaction product. The heterogeneous catalyst of the present invention is prepared by adding a compound of a group VIII metal, preferably rhodium or palladium, to a carrier, preferably α-alumina, kieselguhr or silica, together with an accelerator containing phosphorus or nitrogen, preferably triphenylphosphine. Using the improved catalyst of the present invention also resulted in increased yield of product over conventional methods. The ethylidene diacetate produced using the present method is useful as a starting material for the production of vinyl acetate monomer.

6 Claims, No Drawings

METHODS FOR PREPARING ETHYLIDENE DIACETATE

This is a division of application Ser. No. 07/772,256, filed Oct. 7, 1991 now abandoned.

BACKGROUND OF THE INVENTION

1. Field of the Invention

The present invention relates to a solid catalyst for preparing ethylidene diacetate and to methods for preparing and using that catalyst in a continuous process for manufacturing ethylidene diacetate represented by the following formula:

$$CH_3CH(OCCH_3)_2 \quad\quad (I)$$
$$\phantom{CH_3CH(O}\overset{\displaystyle O}{\underset{\displaystyle \|}{\phantom{C}}}\phantom{CH_3)_2}$$

2. Background of the Invention

Various methods for producing ethylidene diacetate are known in the art. In all of these methods ethylidene diacetate has been prepared in batch reactor systems. Because known processes for preparing ethylidene diacetate employ a homogeneous catalytic reaction, there have been no known attempts to prepare this product by a continuous process. Conventional methods for preparing ethylidene diacetate have used homogeneous catalysts, e.g., transition metals such as rhodium, ruthenium, palladium and platinum. Difficulties arose in separating these homogeneous catalysts from the reaction product.

The most used preparation method employs oxygen to oxidize vaporized acetic acid and ethylene. In another method methyl acetate, carbon monoxide and hydrogen are reacted in a homogeneous catalyst system to yield ethylidene diacetate. This latter method suffers from several significant disadvantages, including the complexity of the reaction process and difficulties associated with separating and purifying the reaction product from the catalyst.

Other prior methods for producing ethylidene diacetate are disclosed in European Patent No. 0028474 and Japanese Patent No. 51-115409. The methods disclosed in these patents also suffer from similar difficulties associated with separating and purifying the product from the catalyst after completion of the reaction. These difficulties also are the result of the ethylidene diacetate being prepared using batch reactor systems.

A continuous method for producing acetic anhydride was disclosed in U.S. Pat. No. 4,046,807. In this method acetic anhydride was synthesized by a continuous process using a supported catalyst containing 13.2 weight percent rhodium and having the formula $RhCl_3 \cdot x\ H_2O\text{-}KI$/activated charcoal. The yield of acetic anhydride using this continuous processing method was 6.76%.

The present invention is the first known continuous processing method capable of synthesizing ethylidene diacetate. The present method employs continuous reaction conditions and has produced yields, based on methyl acetate, of at least 20.4 % under similar conditions to those employed in the '807 patent.

The present invention, by providing a continuous process using a heterogeneous catalyst, both solves the problem of catalyst separation which plagues conventional batchwise processes and produces a better yield than obtained in prior continuous processes for producing acetic anhydride.

SUMMARY OF THE INVENTION

The present invention is directed to a solid catalyst for use in continuous processes for preparing ethylidene diacetate. The catalyst is represented by the following general formula:

$$M_a A_b X \quad\quad (II)$$

wherein M is a compound containing a group VIII transition metal and preferably selected from the group consisting of $(CH_3COO)_2$ Pd and $RhCl(CO)[P(C_6H_5)_3]_2$;

A is an accelerator containing phosphorus or nitrogen and preferably selected from the group consisting of triphenylphosphine, nicotinamide and nicotinic acid; and X is an inorganic carrier preferably selected from the group consisting of kieselguhr, α-alumina, silica, titanium dioxide and activated charcoal;

a is a number between 1 and 5, preferably between 1 and 3, and represents the weight percent based on the catalyst of the transition metal in compound M; and b is a number between 1 and 15 and represents the molar ratio of accelerator A to compound M.

The present invention is further directed to a process for preparing the solid catalyst $M_aA_bX$ useful for preparing ethylidene diacetate. This method includes adding the carrier X, preferably kieselguhr, into a solvent, preferably dichloromethane, in which compound M and accelerator A, preferably triphenylphosphine, have been dissolved, refluxing at a temperature between about 30° C. and about 50° C., distilling under reduced pressure, and drying the residue under vacuum to produce the solid catalyst of formula (2).

The invention further is directed to a process for preparing ethylidene diacetate in a continuous process using a catalyst of formula (2). In the method of the present invention, carbon monoxide, hydrogen, methyl acetate and iodomethane are reacted in the presence of the heterogeneous catalyst (2) and an accelerator. The reaction is carrier out at a temperature between about 90° C. and about 250° C. and at a pressure of about 20–70 atmospheres in a continuous process.

The present invention solves the problems of the prior art related to separation and purification of the reaction product from the catalyst by employing the novel catalyst of general formula (II) supported on an inorganic carrier. The present invention has solved these difficulties by providing a heterogenized catalyst wherein a homogeneous catalyst is supported on an inorganic carrier. As a result, the catalyst of the present invention is easily separated from the reaction product, simplifying separation and purification of the product and of the process as a whole. Further, the present invention simplifies the reaction process by avoiding the necessity for several batch pressing steps. Thus, the present invention results in significant improvement in productivity.

DETAILED DESCRIPTION OF THE INVENTION

In the method of the present invention, ethylidene diacetate was prepared by reacting methyl acetate, iodomethane, carbon monoxide and hydrogen in the presence of a heterogenized catalyst including a group VIII transition element and an inorganic carrier in a fixed bed continuous flow reactor. The catalyst used in the invention retains good catalytic activity after extended usage. The present invention has the advantages of readily and easily producing the desired product in a simplified process using mild reaction conditions.

The catalyst of the present invention has the general formula $M_aA_bX$.

In the composition of the catalyst, compound M contains a group VIII transition metal, preferably selected from the group consisting of palladium and rhodium. The most preferred homogeneous catalyst of a group VIII transition metal used in the present invention is selected from the group consisting of $(CH_3COO)_2Pd$ or $RhCl(CO)[P(C_6H_5)_3]_2$. The metal, preferably rhodium or palladium, is present in the catalyst in an amount from about 1–5 weight percent preferably 1–3 weight percent, based on the catalyst.

The accelerator A contains phosphorus or nitrogen and preferably is selected from the group consisting of triphenylphosphine, nicotinamide and nicotinic acid. The molar ratio of accelerator A to metal in compound M is about 1–15, preferably about 13–15. The accelerator, triphenylphosphine preferably, is present in an amount of about 10–15 weight percent relative to the carrier.

The carrier X is an inorganic compound, preferably selected from the group consisting of kieselguhr, α-alumina, silica, titanium dioxide and activated charcoal. The presently most preferred catalyst is $RhCl(CO)[P(C_6H_5)_3]_2$ $P(C_6H_5)_3$/kieselguhr. The best catalytic activity is shown at about 1.5–2.5 weight percent of rhodium based on the inorganic carrier. The catalyst is preferably prepared by a dipping method at a temperature about 40° C. followed by drying at a temperature of about 120°–150° C. under partial vacuum.

The present inventors have found that a catalyst wherein triphenylphosphine is used as the accelerator and kieselguhr or α-alumina is used as the carrier provides the highest yield of ethylidene diacetate. The control of space velocity in the reactor is a very important condition in preparing ethylidene diacetate and is preferably maintained between about 100–1000 $hr^{-1}$.

The process for preparing ethylidene diacetate used in the present invention is a continuous process and comprises the following steps: a catalytic step wherein the heterogenized catalyst of the present invention is meted with starting materials in a continuous flow reactor; a condensation step wherein the resulting mixture is cooled; and a distillation step wherein the product is separated from the catalyst and any unreacted materials.

The catalyic step, is carried out as a homogeneous catalytic process at an elevated temperature under pressure. The condensation step separates the liquid phase mixture (comprising substantially ethylidene diacetate product) from the vapor phase. Reaction byproducts, e.g., acetic anhydride or acetic acid, may be reused as starting materials for preparing methyl acetate or ethylidene diacetate.

In the preferred methods of the present invention the molar ratio of hydrogen to carbon monoxide is about 1:1 to about 6:1, most preferably about 1:1 to about 3:1. The space velocity of starting materials in the reactor should be maintained at about 100–1,000 $hr^{-1}$, most preferably about 150–800 $hr^{-1}$. The reaction temperature of the reactor should be maintained at about 50°–250° C., most preferably at about 100°200° C. The reaction pressure in the reactor should be maintained at about 10–100 atmospheres, most preferably about 20–70 atmospheres.

The yield, conversion and selectivity of the process of this invention are defined according to the following equations.

Yield(mole %) =

$$\frac{\text{(moles of ethylidene diacetate produced)}}{\text{(moles of methyl acetate feed)}} \times 100\%$$

Conversion(mole %) =

$$\frac{\text{(moles of methyl acetate reacted)}}{\text{(moles of methyl acetate feed)}} \times 100\%$$

Selectivity(mole %) =

$$\frac{\text{(moles of ethylidene diacetate produced)}}{\text{(moles of methyl acetate reacted)}} \times 100\%$$

The starting materials and products were quantitatively analyzed using gas chromatography from correlation curves obtained using anisole as the standard material to reactants and products.

The present invention will be illustrated in more detail by the following examples.

Preparation of the Catalyst

The following examples 1–7 illustrate preparation of catalysts in accord with the present invention.

EXAMPLE 1

6.8 g of kieselguhr dried in a vacuum desiccator at 150° C., 0.72 g (0.76 mmole) of $RhCl(CO)[P(C_6H_5)_3]_2$, and 3.10 g (12.0 mmole) of triphenylphosphine were added to 30 ml of dichloromethane. The reaction mixture was refluxed for 30 minutes, the solvent was distilled off under vacuum, and the residue was dried in a vacuum desiccator for 24 hours to prepare a catalyst of $RhCl(CO)[P(C_6H_5)_3]_2 \cdot P(C_6H_5)_3$/kieselguhr containing 1.13 weight percent rhodium. The ratio of molar triphenylphosphine to Rh compound is 11.54.

EXAMPLE 2

The procedure of Example 1 was followed except that the reactants were 6.8 g of α-alumina, 1.03 g (1.499 mmole) of $RhCl(CO)[P(C_6H_5)_3]_2$ and 3.0 g (11.43 mmole) of triphenylphosphine. A catalyst of $RhCl(CO)[P(C_6H_5)_3]_2 \cdot P(C_6H_5)_3$/α-alumina containing 1.6 weight percent rhodium was produced. The molar ratio of triphenylphosphine to Rh compound is 7.63.

EXAMPLE 3

The procedure of Example 1was repeated except that the reactants were 9.3 g of α-alumina, 2 g (2.89 mmole) of $RhCl(CO)[P(C_6H_5)_3]_2$ and 3.0 g (11.43 mmole) of triphenylphosphine. A catalyst of $RhCl(CO)[P(C_6H_5)_3]_2 \cdot P(C_6H_5)_3$/α-alumina containing 2.2 weight percent rhodium was produced. The molar ratio of triphenylphosphine to Rh compound is 3.96.

EXAMPLE 4

The procedure of Example 1 was repeated except that the reactants were 9.80 g of $TiO_2$, 3.24 g (4.69 mmole)of $RhCl(CO)[P(C_6H_5)_3]_2$ and 5 g (40.60 mmole) of nicotinamide. A catalyst of $RhCl(CO)[P(C_6H_5)_3]_2 \cdot$ nicotinamide/$TiO_2$ containing 3.2 weight percent rhodium was produced. The molar ratio of triphenylphosphine to Rh compound is 8.66.

EXAMPLE 5

The procedure of Example 1 was repeated except that the reactants were 9.80 g of $TiO_2$, 3.24 g (4.69 mmole) of $RhCl(CO)[P(C_6H_5)_3]_2$ and 5 g (40.60 mmole) of nicotinic acid. A catalyst of $RhCl(CO)[P(C_6H_5)_3]_2$. nicotinic acid/$Ti_2$ containing 3.2 weight percent rhodium was produced. The molar ratio or nicotinic acid to Rh compound is 8.66.

EXAMPLE 6

The procedure of Example 1 was repeated except that the reactants were 9.64 g of kieselguhr, 3.87 g (17.2 mmole) of $(CH_3COO)_2Pd$ and 3 g (11.43 mmole) of triphenylphosphine. A catalyst of $(CH_3COO)_2Pd.P(C_6H_5)_3$/kieselguhr containing 3.5 weight percent palladium was produced. The molar ratio of triphenylphosphine to Pd compound is 0.66

EXAMPLE 7

The procedure of Example 1 was repeated except that the reactants were 6.80 g of kieselguhr and 1.2 g (1.74 mmole) of $RhCl(CO)[P(C_6H_5)_3]_2$. A catalyst of $RhCl(CO)$ $[P(C_6H_5)_3]_2$/kieselguhr containing 1.6 weight percent rhodium was produced. The molar ratio of triphenylphosphine to Rh compound 6.90

Preparation of Ethylidene Diacetate

The following examples illustrate the preparation of ethylidene diacetate using catalysts prepared in accord with the present invention.

EXAMPLE 8

In a continuous, fixed bed stainless steel flow reactor having an inner diameter of 1.2 cm and a length of 30 cm, methylacetate fed at the rate of 0.0234 ml/min and iodomethane fed at the rate of 0.0066 ml/min were reacted continuously in the presence of the catalyst prepared in Example 1, under the reaction conditions of 300 $hr^{-1}$ space speed, 54 atmospheres pressure, and with a mixed gas having a molar ratio of hydrogen to carbon monoxide of 3:1. The resulting reaction mixture was cooled, condensed and analyzed by gas chromatography.

The results of the gas chromatographic analysis of the reaction products are shown in Table 1.

TABLE 1

| Reaction temperature (°C.) | Reaction time (hr) | Conversion (%) | Yield (%) | | | Selectivity (%) | | |
|---|---|---|---|---|---|---|---|---|
| | | | *ED | Acetic anhydride | Acetic acid | *ED | Acetic anhydride | Acetic acid |
| 100 | 6 | 21.0 | 4.9 | 0 | 15.9 | 23.8 | 0 | 76.2 |
| 140 | 6 | 40.3 | 5.2 | 0 | 54.5 | 8.7 | 0 | 91.3 |

*Ethylidene Diacetate

EXAMPLE 9

The procedure of Example 8 was repeated, except that the catalyst prepared in Example 2 was used as the catalyst.

The results of the gas chromatographic analysis of the reaction products are shown in Table 2.

TABLE 2

| Reactants (ml/min) | | Reaction pressure (atm) | Space Velocity ($hr^{-1}$) | Reaction temp (°C.) | Reaction time (hr) | Conversion (%) | Yield (%) | | | Selectivity (%) | | |
|---|---|---|---|---|---|---|---|---|---|---|---|---|
| Methyl acetate | Iodo methane | | | | | | *ED | Acetic anhydride | Acetic acid | *ED | Acetic anhydride | Acetic acid |
| 0.0312 | 0.088 | 54 | 260 | 140 | 1 | 60.7 | 3.4 | 0 | 57.3 | 5.6 | 0 | 94.4 |
| | | | | | 2 | 43.0 | 6.7 | 9.5 | 26.8 | 9.5 | 22.1 | 62.3 |
| | | | | | 3 | 60.9 | 7.8 | 12.9 | 40.2 | 12.9 | 21.2 | 66.0 |
| | | | | | 4 | 50.2 | 8.4 | 16.7 | 0 | 41.8 | 88.3 | 0 |

*Ethylidene Diacetate

EXAMPLE 10

The procedure of Example 8 was repeated, except that the catalyst of example 3 was used as the catalyst.

The results of the gas chromatographic analysis of the reaction products are shown in Table 3.

TABLE 3

| Reactants (ml/min) | | Reaction pressure (atm) | Space Velocity ($hr^{-1}$) | Reaction temp (°C.) | Reaction time (hr) | Conversion (%) | Yield (%) | | | Selectivity (%) | | |
|---|---|---|---|---|---|---|---|---|---|---|---|---|
| Methyl acetate | Iodo methane | | | | | | *ED | Acetic Anhydride | Acetic acid | *ED | Acetic anhydride | Acetic acid |
| 0.0234 | 0.0066 | 74 | 225 | 140 | 1 | 51.5 | 6.3 | 1.3 | 43.8 | 12.3 | 2.6 | 85.1 |
| | | | | | 2 | 32.3 | 2.3 | 0 | 30.1 | 6.9 | 0 | 93.1 |
| | | | | | 3 | 24.7 | 3.5 | 0 | 21.2 | 14.3 | 0 | 85.7 |
| | | | | | 4 | 37.8 | 12.7 | 7.3 | 17.8 | 33.6 | 19.3 | 47.1 |
| | | | | | 5 | 33.9 | 11.8 | 7.4 | 7.4 | 34.8 | 21.8 | 43.4 |
| | | | | | 14 | 30.3 | 11.2 | 5.8 | 5.8 | 37.0 | 19.1 | 43.9 |
| | | | | | 20 | 17.6 | 7.0 | 10.1 | 10.1 | 41.1 | 58.9 | 0 |
| | | | | 160 | 2 | 19.0 | 6.3 | 12.6 | 12.6 | 33.2 | 66.8 | 0 |
| | | | | | 4 | 23.6 | 4.6 | 5.9 | 5.9 | 19.7 | 25.3 | 55.0 |

*Ethylidene Diacetate

EXAMPLE 11

The procedure of Example 8 was repeated, except that the catalyst of Example 4 was used as the catalyst.

The results of the gas chromatographic analysis of the reaction products are shown in Table 4.

TABLE 4

| Reactants (ml/min) | | Reaction pressure (atm) | Space Velocity (hr$^{-1}$) | Reaction temp (°C.) | Reaction time (hr) | Conversion (%) | Yield (%) | | | Selectivity (%) | | |
|---|---|---|---|---|---|---|---|---|---|---|---|---|
| Methyl acetate | Iodo methane | | | | | | *ED | Acetic anhydride | Acetic acid | *ED | Acetic anhydride | Acetic acid |
| 0.0117 | 0.0033 | 45 | 150 | 140 | 14 | 29.1 | 1.7 | 0 | 28.3 | 2.6 | 0 | 97.4 |
| | | | | 150 | 2 | 29.1 | 3.6 | 7.8 | 17.7 | 12.5 | 26.8 | 60.7 |
| | | | | | 4 | 29.7 | 2.8 | 7.8 | 19.0 | 9.6 | 26.3 | 64.1 |
| | | | | | 6 | 36.6 | 6.7 | 9.5 | 20.3 | 18.8 | 26.1 | 55.6 |
| | | | | | 8 | 34.2 | 6.8 | 9.3 | 18.2 | 19.9 | 27.1 | 53.0 |
| | | | | | 12 | 26.7 | 8.8 | 0 | 18.0 | 32.8 | 0 | 67.2 |
| | | | | | 23 | 36.2 | 7.8 | 11.5 | 16.9 | 21.5 | 31.8 | 46.7 |

*Ethylidene Diacetate

EXAMPLE 12

The results of the gas chromatographic analysis of the reaction products are shown in Table 7.

TABLE 7

| Reactants (ml/min) | | Reaction pressure (atm) | Space Velocity (hr$^{-1}$) | Reaction temp (°C.) | Reaction time (hr) | Conversion (%) | Yield (%) | | | Selectivity (%) | | |
|---|---|---|---|---|---|---|---|---|---|---|---|---|
| Methyl acetate | Iodo methane | | | | | | *ED | Acetic anhydride | Acetic acid | *ED | Acetic anhydride | Acetic acid |
| 0.0075 | 0.0075 | 67 | 220 | 170 | 2 | 10.5 | 1.4 | 0 | 9.1 | 13.8 | 0 | 86.2 |
| | | | | | 4 | 7.8 | 1.1 | 0 | 6.7 | 13.9 | 0 | 86.1 |
| | | | | 190 | 2 | 34.5 | 1.3 | 1.1 | 32.1 | 3.8 | 3.1 | 93.1 |
| | | | | | 4 | 36.8 | 1.2 | 8.7 | 26.9 | 23.7 | 23.7 | 73.0 |
| | | | | 200 | 2 | 61.4 | 0.7 | 8.5 | 52.1 | 13.9 | 13.9 | 84.9 |
| | | | | | 4 | 65.9 | 1.4 | 9.1 | 55.4 | 13.8 | 13.8 | 84.0 |

*Ethylidene Diacetate

The procedure of Example 8 was repeated, except that the catalyst of Example 5 was used as the catalyst.
The results of the gas chromatographic analysis of the reaction products are shown in Table 5.

EXAMPLE 15

The procedure of Example 8 was repeated, except that RhCl(CO)[P(C$_6$H$_5$)$_3$]$_2$./kieselguhr containing 2.46 weight percent rhodium was used as the catalyst.
The results of the gas chromatographic analysis of the reaction products are shown in Table 8.

TABLE 5

| Reactants (ml/min) | | Reaction pressure (atm) | Space Velocity (hr$^{-1}$) | Reaction temp (°C.) | Reaction time (hr) | Conversion (%) | Yield (%) | | | Selectivity (%) | | |
|---|---|---|---|---|---|---|---|---|---|---|---|---|
| Methyl acetate | Iodo methane | | | | | | *ED | Acetic anhydride | Acetic acid | *ED | Acetic anhydride | Acetic acid |
| 0.0117 | 0.0033 | 67 | 150 | 170 | 2 | 34.4 | 1.01 | 3.01 | 30.3 | 2.9 | 8.9 | 88.2 |

*Ethylidene Diacetate

EXAMPLE 13

The procedure of Example 8 was repeated, except

TABLE 8

| Reactants (ml/min) | | Reaction pressure (atm) | Space Velocity (hr$^{-1}$) | Reaction temp (°C.) | Reaction time (hr) | Conversion (%) | Yield (%) | | | Selectivity (%) | | |
|---|---|---|---|---|---|---|---|---|---|---|---|---|
| Methyl acetate | Iodo methane | | | | | | *ED | Acetic anhydride | Acetic acid | *ED | Acetic anhydride | Acetic acid |
| 0.015 | 0.015 | 67 | 450 | 140 | 2 | 58.5 | 3.9 | 12.1 | 42.5 | 6.7 | 20.7 | 72.6 |
| | | | | | 4 | 60.1 | 18.5 | 12.9 | 28.6 | 30.8 | 21.6 | 47.6 |
| | | | | | 6 | 56.7 | 20.4 | 6.7 | 29.7 | 35.9 | 11.8 | 52.3 |

*Ethylidene Diacetate that the catalyst of Example 6 was used as the catalyst.
The results of the gas chromatographic analysis of the reaction products are shown in Table 6.

EXAMPLE 16

The procedure of Example 8 was repeated, except

TABLE 6

| Reactants (ml/min) | | Reaction pressure (atm) | Space Velocity (hr$^{-1}$) | Reaction temp (°C.) | Reaction time (hr) | Conversion (%) | Yield (%) | | | Selectivity (%) | | |
|---|---|---|---|---|---|---|---|---|---|---|---|---|
| Methyl acetate | Iodo methane | | | | | | *ED | Acetic anhydride | Acetic acid | *ED | Acetic anhydride | Acetic acid |
| 0.0117 | 0.0033 | 67 | 150 | 170 | 8 | 62.5 | 1.81 | 0 | 60.6 | 2.9 | 0 | 97.1 |

*Ethylidene Diacetate

EXAMPLE 14

The procedure of Example 8 was repeated, except that the catalyst of Example 7 was used as the catalyst.

that RhCl(CO)[P(C$_6$H$_5$)$_3$]$_2$/divinyl benzene polystyrene resin containing 1.96 weight percent rhodium (Strem) was used as the catalyst.
The results of the gas chromatographic analysis of the reaction products are shown in Table 9.

TABLE 9

| Reactants (ml/min) | | Reaction pressure (atm) | Space Velocity (hr$^{-1}$) | Reaction temp (°C.) | Reaction time (hr) | Conversion (%) | Yield (%) | | | Selectivity (%) | | |
|---|---|---|---|---|---|---|---|---|---|---|---|---|
| Methyl acetate | Iodo methane | | | | | | *ED | Acetic anhydride | Acetic acid | *ED | Acetic Anhydride | Acetic acid |
| 0.0117 | 0.0033 | 67 | 150 | 170 | 2 | 34.4 | 1.01 | 3.05 | 30.3 | 2.9 | 8.9 | 88.2 |

*Ethylidene Diacetate

The present invention benefits from the following advantages: the reaction is carried out in a continuous process, the produced ethylidene diacetate is easily purified because the catalyst is not mixed with the reaction product, the process saves energy because no distillation step is necessary and the time required for production is lessened.

The foregoing description of the invention has been directed in primary part to a particular preferred embodiment and method in accordance with the requirements of the patent statutes and for purposes of explanation and illustration. It will be apparent, however, to those skilled in the art that many modifications and changes in the specifically described catalysts and methods may be made without departing from the scope and spirit of the invention. Therefore, the invention is not restricted to the particular catalysts and methods illustrated and described, but covers all modifications which may fall within the scope of the following claims.

It is Applicants' intention in the following claims to cover such modifications and variations as fall within the true spirit and scope of the invention.

What is claimed is:

1. A process for preparing ethylidene diacetate by a continuous reaction comprising continuously reacting at a temperature between about 90°–250° C. and a pressure between about 20–70 atmospheres, methyl acetate, iodomethane, carbon monoxide and hydrogen wherein the molar ratio of hydrogen to carbon monoxide is maintained between about 1:1 and about 6:1, said reaction occuring in the presence of a catalyst system having the formula $M_aA_bX$ wherein, M is a compound of a group VIII transition metal which catalyzes the production of ethylidene diacetate;

A is an accelerator containing nitrogen or phosphorus;

X is an inorganic carrier;

"a" is a number between 1 and 5 and represents the weight percent of metal in said compound M based on said catalyst system; and "b" is a number between 1 and 15 and represents the molar ratio of said accelerator A to said compound M.

2. The process according to claim 1 wherein the molar ratio of hydrogen to carbon monoxide is between about 1:1 and about 3:1.

3. The process according to claim 2 wherein the space velocity of reactants is between about 150–1,000 hr$^{-1}$.

4. The process according to claim 1 wherein the concentration of iodomethane is about 20–70 weight percent based on total reactants.

5. The process according to claim 1 wherein said compound M is selected from the group consisting of $(CH_3COO)_2Pd$ and $RhCl(CO)[P(C_6H_5)_3]$, said accelerator A is selected from the group consisting of triphenylphosphine, nicotinamide and nicotinic acid, and said carrier X is selected from the group consisting of kieselguhr, α-aluminia, silica, titanium dioxide and activated charcoal.

6. The process according to claim 1 wherein said compound M is $RhCl(CO)[P(C_6H_5)_3]$, said accelerator A is triphenylphosphine and said carrier X is kieselguhr.

* * * * *